United States Patent [19]
Dechene et al.

[11] Patent Number: 5,302,896
[45] Date of Patent: Apr. 12, 1994

[54] MAGNETIC RESONANCE ANALYSIS IN REAL TIME INDUSTRIAL USAGE MODE

[75] Inventors: Ronald L. Dechene, Boxford, Mass.; Thomas B. Smith, Atkinson, N.H.; Scott A. Marino, Haverhill; Ajoy K. Roy, Danvers, both of Mass.

[73] Assignee: Auburn International, Inc., Danvers, Mass.

[21] Appl. No.: 794,931

[22] Filed: Nov. 20, 1991

[51] Int. Cl.$^5$ ............................................. G01R 33/20
[52] U.S. Cl. .................................... 324/307; 324/300
[58] Field of Search ............... 324/300, 307, 309, 310, 324/311, 312, 313, 314, 318, 322; 128/653 A

[56] References Cited
U.S. PATENT DOCUMENTS

| | | | |
|---|---|---|---|
| 5,015,954 | 5/1991 | Dechene et al. | 324/307 |
| 5,049,819 | 9/1991 | Dechene et al. | 324/307 |

Primary Examiner—Michael J. Tokar
Attorney, Agent, or Firm—Jerry Cohen; Edwin H. Paul

[57] ABSTRACT

Pulsed NMR system for industrial measurements comprising sample throughout system (P, LI, V1, V2) and user system controls (104) to establish digitized free induction decay curves (C), from which Abragam, Gaussian and exponential components are determined using a Marquardt-Levenberg iteration technique, and using regression techniques to correlate the curve components to the target nuclei.

19 Claims, 8 Drawing Sheets

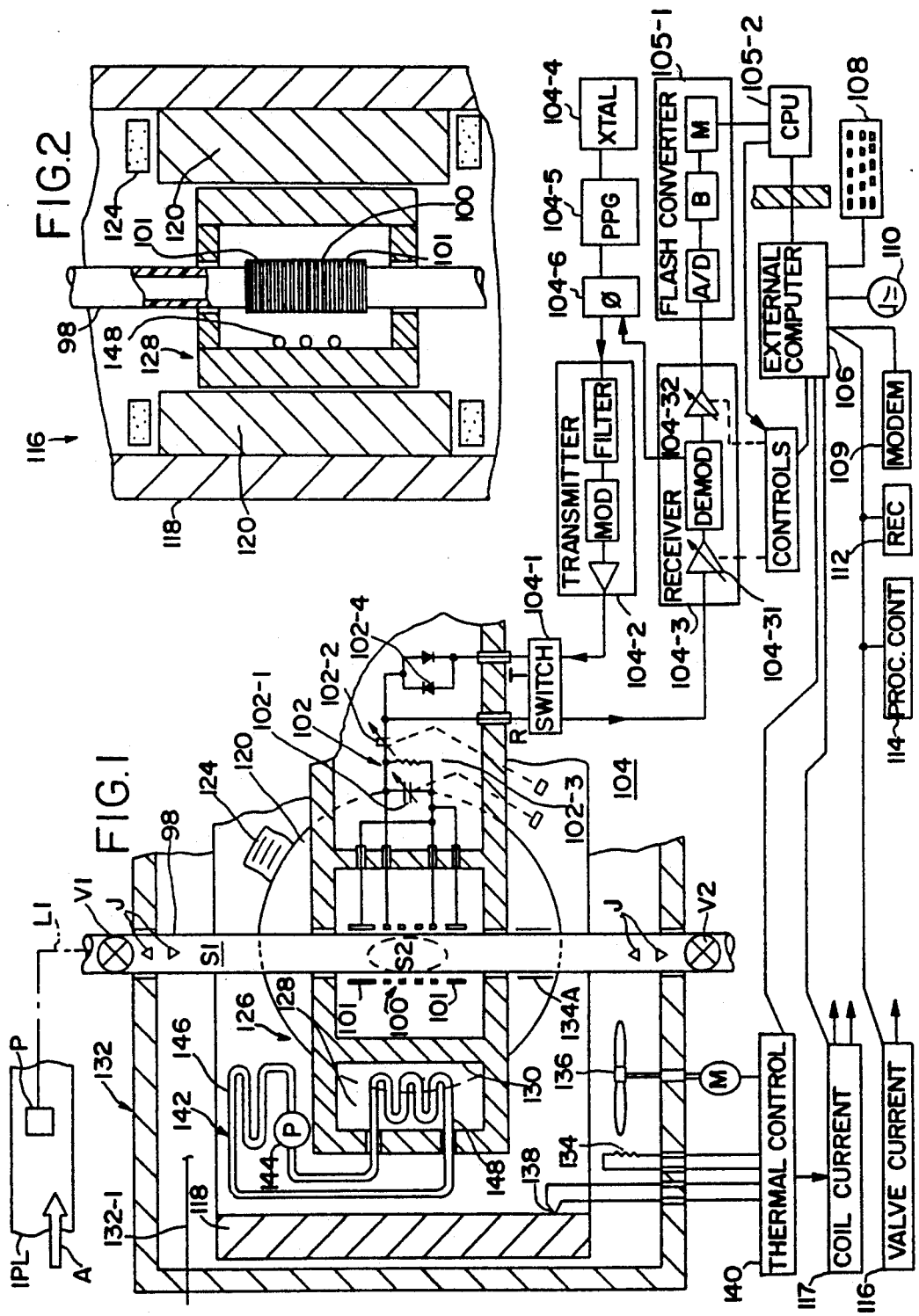

MAGNETIC RESONANCE ANALYSIS IN REAL TIME INDUSTRIAL USAGE MODE

CROSS REFERENCE TO RELATED APPLICATIONS

This application is closely related to the U.S. Pat. No. 5,015,954 issued on May 14, 1991 to Dechene et al., and to U.S. Pat. No. 5,049,819 granted Sep. 17, 1991 to Dechene et al., both entitled "Magnetic Resonance Analysis in Real Time, Industrial Usage Mode". Both of these patents are of common assignment with this application, and the disclosures of both are hereby incorporated herein by reference, as though set out at length herein.

FIELD OF THE INVENTION

The present invention relates to an instrument for measurement of the type and quantity of lattice bound and free magnetically active nuclei within successive samples of a process material flow through pulsed nuclear magnetic resonance (NMR) techniques and more particularly the application of such measurement to industrial process control of moisture content, polymer content, crystallinity fraction, oil/fat fraction and other percentages of components analysis and other parameters.

BACKGROUND OF THE INVENTION

NMR techniques have grown extensively over the past forty years, most notably in the medical instrumentation areas where in vivo examination of various parts of the human body can be seen, and in clinical research laboratory uses. In addition there has been some use and interest in the application of these techniques to industrial instrumentation and control tasks. The present invention enables effective utilization (technically and economically) of pulsed NMR techniques in industrial areas to replace or complement existing optical and radiant energy-based and chemical-based and other (e.g. mechanical) instrumentation.

The following is a brief review of nmr [NMR] theory and concepts pertinent to understanding the present invention. [The term "magnetic resonance imaging" (MRI) is an alternative, interchangeable name for "nuclear magnetic resonance" (NMR).] Approximately one third of the elemental isotopes and certain compounds with non-zero spin quantum numbers are magnetically active and suitable for [MRI] nmr detection.

In a simplified model, a spinning isolated nucleus will align itself either with or against a static magnetic field. There will be a nearly equal number of nuclei aligned in each direction since there is only a small energy difference between these two states so a thermal equilibrium exists between these two states. However, statistically there will be a small number of excess nuclei which give rise to nmr signals. The term "nuclei" will subsequently refer only to magnetically active nuclei.

Nuclei in a magnetic field will precess similar to a spinning top because there is an angular acceleration provided by the interaction of the magnetic field and the magnetic moment of the nuclei. This precession occurs in the direction of the magnetic field. Quantum mechanics shows that only a selected number of possible alignments is possible. The precessional frequency is determined by which alignment occurs and the magnetic properties of the nucleus being studied. The fundamental nmr signal is derived from inducing transitions between these different alignments. This is often done by using the magnetic component of an applied RF (radio frequency) signal. When this component is applied perpendicularly to the magnetic field a resonance occurs at a particular RF frequency where transitions between the different alignments happen. This resonance typically occurs in the megahertz frequency ranges when a strong magnetic field is used. This field is in the 1 Tesla (10,000 Gauss) order of magnitude. Resonance being defined as the condition such that, after a short pulse of energy is applied to the sample and a return pulse of decaying energy is generated by the sample, the return signal is essentially an infinite wavelength of a beat frequency product of demodulated excitation and return signals. There are other well understood definitions of resonance known in the art.

Pulsed NMR spectroscopy is described in our above-cited patents. This technique uses a burst or pulse which is designed to excite the nuclei of a particular nuclear species of a sample being measured (the protons, or the like, of such sample having first been precessed in an essentially static magnetic field); in other words the precession is modified by the pulse. After the application of the pulse there occurs a free induction decay (FID) of the magnetization associated with the excited nuclei. Traditional Fourier Transform analysis generates a frequency domain spectrum which can be used to advantage in studying the nuclei of interest. The duration of the pulses, the time between the pulses, the pulse phase angle and the composition of the sample are parameters which affect the sensitivity of this technique. These frequency domain techniques are not easily useable in industrial applications, especially on-line applications.

An object of this invention is an improved measurement system which leads to accurate, fast determination of the types and quantity of the nuclear species of interest.

A further object of this invention is its application to the industrial, on-line problems of measuring and calibrating the controlling processes per se.

Another object of this invention is to utilize time domain analysis in achieving such system.

The principal variables of interest are moisture, oil/fat and polymer crystallinity and density. But other parameters can be measured based on hydrogen or other sensitive species including e.g. sodium and fluorine. It is an object of this invention to accommodate a variety of such measuring tasks.

Another object is to accommodate the dynamics of industrial on-line applications including variations of density, temperature, packing and size factors, friction and static electricity, vibrations and frequent, repetitive, cyclic and non-cyclic measurements.

A further object of the invention is to integrate all the features of accurate, fast determination of the types and quantity of the nuclear species of interest, the use of time domain analysis in such a system, its application to the industrial, on-line problems of monitoring and controlling processes, measuring free and bound water in organic or inorganic substances (based on hydrogen nuclei modified-precession analysis) and other parameter measurement (based on hydrogen or other sensitive species including e.g. fluorine, sodium-23, etc.) accommodating the dynamics of industrial on-line applications including variations of density, temperature, packing and size factors, friction and static electricity, vibration and frequent, repetitive, cyclic and non-cyclic measurements.

A further object of the invention is to use such magnetic resonance techniques in polymer analysis, including crystallinity and density, all with enhanced accuracy and reliability of data obtained and while achieving the necessary practical economies.

A further object of the present invention is to extend those achievements further in relation to industrial on-line processing, and the like, as applied to mixed species (or mixed phases) of NMR-active materials and more particularly foodstuffs and plastics materials (and being applicable to many other NMR-active materials) with a third component such as oils/fats or solvents in addition to two main components (moisture/solids, crystalline/amorphous).

SUMMARY OF THE INVENTION

The present invention provides a materials measurement system using magnetic resonance hardware, controls (and related data capture and data reduction means and steps) and techniques, preferably in the time domain. The system can be used to capture data from a continuous production line or like repetitive measurements system.

The NMR system effects a reliable extraction of free induction decay data in a way that is practical in an industrial on-line context and economically practical. The system is characterized by provision of a base magnetic field homogeneity to a reasonable degree and offset of inhomogeneity effects, temperature stabilization to a reasonable degree and offsets of thermal drift effects and use of multiple runs (10–50) for each measurement with digital data reduction and use of statistical methods or other data manipulation for industrially effective measurement. These data can be represented, for discussion/analysis, as a free induction decay curve (FID) with attention to time sequence components of a first, very fast, modified Gaussian (G) (a Gaussian multiplied by a sinc function sometimes called an Abragam function) followed by a slower essentially Gaussian region in turn followed by an even slower exponential region. These different regions are representative of proton relaxation after an initial excitation by a pulse of transmitted and near resonant coupled radio frequency energy that induces a modification of the precession of protons in the sample being measured in a high static magnetic field. There may be cases where the number of regions is other than three e.g. two (an Abragam and an exponential). In addition, it is possible that a region is represented by a function other than the Abragam, G, and exponential mentioned above. The calibration system including the Marquardt-Levenberg (M-L) technique described below will still be applicable.

The Abragam FID portion is based on measurement of data points of magnetization decay of immobile or highly constrained protons (as in crystalline structures) present in the sample and picked up at the NMR system's receiver; this portion is usually based on the response of bound proton species such as the hydrogen or hydrate content of chemical compounds (or similarly for many other NMR-active species, e.g. fluorine or sodium-23, which are chemically bonded and highly constrained). The slower Gaussian region is a transition zone between the constrained and the loosely bound protons. The slow exponential FID portion is usually based on loosely constrained or unconstrained NMR-active species such as moisture physically present in a sample but essentially chemically unbonded thereto. The Abragam, Gaussian and exponential FID portions and the FID as a whole can be extrapolated to a decay origin usually set close to the time center of the excitation pulse. Zero time intercepts of these curves (i.e., FID and one or more of its component curve portions) provide ratio data using the FID intercept and/or intercepts of one or more of the curve portions to determine e.g. free vs. bound water in a moist material (e.g. for process control of industrial chemicals, minerals and metals, agricultural commodities, processed foods by determining moisture content for upstream or downstream correction or for acceptance/rejection purposes). Instead of determining moisture in, say a food product the object may be to determine ratio of relatively crystalline and non-crystalline components of a material, e.g. hard and soft components of a plastic material and that is accomplished in a fashion analogous to the moisture measurement. Polymer crystallinity and density can also be determined through the invention because the FID varies predictably as a function of crystallinity and density.

Also oils, fats and solvents may appear in foods, and residual solvents may appear in plastics or other industrial materials as an error factor to be resolved and/or as a target parameter to be measured. The NMR response of such solvent or oil/fat portion can be isolated by the present invention, and to some degree sub-components of such solvents or oils/fats may appear as additional very slowly decaying exponential regions in the calibration system described herein.

The measuring system of the invention comprises economically scaled down and industrially hardened portions, relative to the widely used laboratory systems. A magnetic essentially fixed field comprises closely spaced pole pieces with a 4,000–8,000 Gauss field (about 4,700 Gauss, nominally). Helmholtz coils are provided which are adjustable to provide rapid adjustments for the precise, correct field and overlaid with coarse, slower adjustments to thermal environment. This is to assure that the product of a materials related constant (gamma) multiplied by the magnetic field strength, which is resonant frequency, will match excitation frequency by a selected offset. Still further fine adjustment is made in signal processing as described below.

The present invention accommodates great streams of data in practical ways through features, described below, which are inter-related to the thermal controls to provide a measuring system meeting the foregoing objects. The materials of construction are also integrated into the reliability considerations, as described below. Measurement of a sample is often accomplished in approximately a minute (in contrast to hours-long measurements of many prior art systems).

The measurements made through the present invention based on ratios of intercepts and/or integrated areas under curves and/or peak analysis are independent of weight or volume of sample or gain of the system in a measuring region whereas precise weight measurement is a necessary feature—and limitation of—many prior art systems.

Prior art efforts at industrial on-line measurement of the same parameters as are treated herein have involved non-NMR gravimetric, radioactive, acoustic, optical and electrostatic/capacitive systems, none wholly satisfactory for present purpose and NM usage in support of continuous industrial processes has been a forcing of off-line laboratory instruments into service (at great expense and nevertheless with inadequate sampling) or some early efforts of the 1980's at industrially hardened pulsed NMR instruments making use of only one or two data points for FID analysis. The present invention breaks out of all those dead ends.

Laboratory methods of frequency domain NMR analysis are described for crystallinity content determination in, e.g., Spiess, "Molecular Dynamics of Solid Polymers As Revealed By Deuteron NMR", 261 Colloid & Polymer Science 193–209 (1983) and Kauffman et al., "Determination of Transition Temperatures and Crystalline Content of Linear High Molecular-Weight Polyethylene by Proton NMR Spectroscopy", 27 Jl. of Polymer Science 2203–2209 (1989). Time domain analysis using pulsed and multiple pulsed NMR free induction decay in coals for detection of free radicals therein is shown in the laboratory systems of Gerstein et al. (Iowa State University Ames Laboratory) reported in "Utility of Pulsed Nuclear Magnetic Resonance In Studying Protons In Coals", 81 Jl. of Phys. Chem. 566–571 (1977) and "1H Nuclear Magnetic Resonance Studies of Domain Structures In Polymers", 52(9) J. Appl. Phys. 5517–5528 (1981). The instruments or former instruments of IBM Federal Systems Division and Brucker GmbH (model P201) and the description in U.S. Pat. No. 4,430,719, granted Feb. 7, 1984, to Pearson are the earlier attempts referred to above as industrial use of NMR methods. The Pearson work was embodied in 1985 industrial plant control work of Kaiser Aluminum & Chemical Corp. It was not effective as a reliable quantitative device. Auburn International, Inc. offered the Pearson/Kaiser product for sale in 1987–1988 and it could not meet the needs of industrial on-line monitoring. These failures were followed by the making of the inventions of the above cited Dechene et al. patents and these as enhanced through the present invention, all solve the industrial on-line problem for various materials.

Other objects, features, and advantages will be apparent from the following detailed description of preferred embodiments taken in conjunction with the accompanying drawing(s) in which:

BRIEF DESCRIPTION OF THE DRAWING (S)

FIGS. 1 and 2 are lateral and cross-sections of a preferred embodiment of the invention including electrical block diagram components.

DETAILED DESCRIPTION OF PREFERRED EMBODIMENTS

Figure 3:
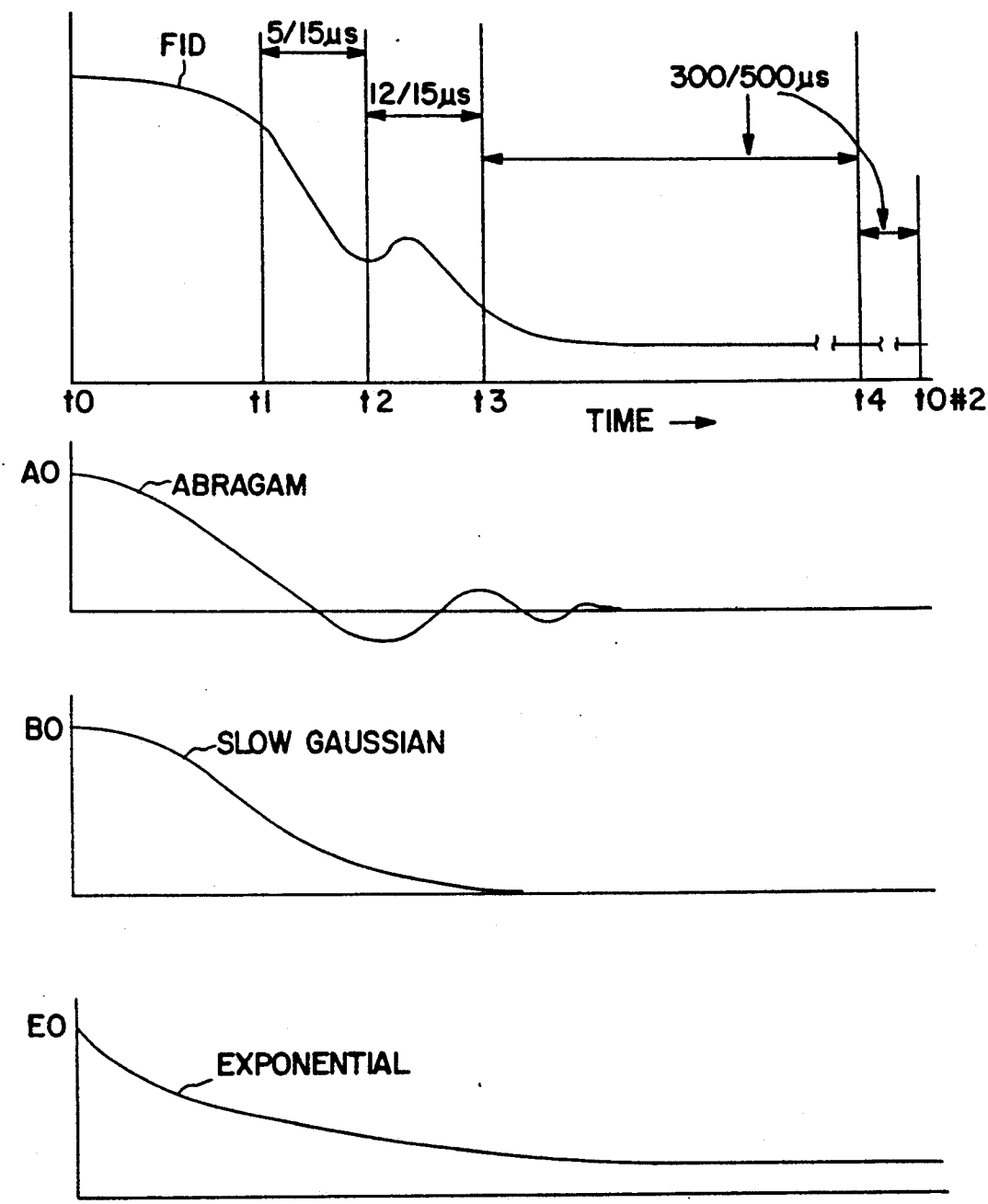
FIG. 3 shows the voltage-time wave forms of the free induction decay (FID) of the embodiment of FIGS. 1-2 in the course of operation.

FIGS. 1–2 show transverse and cross sections with block diagram inserts of a first embodiment of the apparatus and method of the invention. An industrial process line IPL has material flowing as indicated by arrow A. Some of the material is captured by a probe P and fed through an inlet line LI to a sample region S1. The said region is defined by a tube 98 typically about 30 cm long made of an essentially non-magnetic, nonconducting material which does not itself generate substantially interfering FID signals (glass, certain ceramics, certain plastics or hybrids). The sample region is defined between inlet and outlet valves V1 and V2. Gas jets J are also provided. These are pulsed on/off repeatedly to agitate fluent sample materials during sample admission and expulsion. The region S2 is the critical portion of the sample. It is surrounded by a sample coil 100 tuned to resonance and driven by a tuning circuit 102 and related transmitter/receiver controller 104. Grounded loops 101 are Lenz Law shields which are provided above and below coil 100 to help shape the field of coil 100—i.e., contain the field established by an excitation pulse. The controller 104 includes an on-board microprocessor and required power supply elements, memory, program and I/O decoding suitable to interconnect to the hardware shown and to an external microcomputer 106 with keyboard 108, monitor (or other display) 110, recorder 112 and/or process controller 114 (to control the process at IPL). The operator initiates and controls operation from the display keyboard 108 and the resulting data and signals are subsequently shown on the display 100 and utilized in 110, 112 and/or 114. The computer 106 also controls instrument operation conditions.

The region S2 of tube 98 and coil 100 are in a static, but adjustable, crossing magnetic field defined by a magnetic assembly 116 which comprises a yoke 118, pole pieces 120, surrounding Helmholtz coils 124, and a coil current generator 117. The critical sample region S2 of the tube 98 and magnet are contained in a metallic (but non-ferromagnetic) box 126 with highly thermally conductive face-plates 128 and internal partitions 130 and over-all mass related to each other to minimize harmonics and other interferences with a signal emitted from coil 100 to a sample and/or returned from the sample for pick-up by coil 100 and its tuned circuit 102 and transmit/receive controller 104.

The magnetic assembly 116 including yoke 118, and other parts therein as shown on FIGS. 1–2, is in turn contained in an environmental control chamber 132 with optional inert gas fill and purge controls (not shown), an internal gas heater 134, a motor M driving fan 136, and a temperature sensor 138 which can be applied to the yoke or other detection region whose temperature is reflective of the temperature at pole pieces 120 and in the sample region therebetween. A thermal controller 140 processes temperature signals from 138 to adjust heating/circulation at 134/136 as a coarse control and to adjust current through the Helmholtz coils 124 at magnet pole pieces 120 as a sensitive and fast fine control, as well as implementing general control instructions of computer 106. Further thermal stabilization may be provided by a closed loop heat exchanger 142 having pump 144 and coils 146 attached to yoke 118 and coils 148 attached to the plates 128 of box 126.

The strength, consistency and constancy of the magnetic field between poles 120 in the region S2 of the sample is thus controlled by a uniform base magnetic field in the entire region S2. The Helmholtz coils 124 are energized by the coil current controller 117 to accurately trim the final magnitude of the field in which the sample is placed. This field is the vector addition of the fields due to the magnet poles 120 and the Helmholtz coils 124. The controller 117 sets the current through the Helmholtz coils 124 using current generators. The coils 124 are wound around the magnet pole pieces such that the magnetic field created by the current in the coils 124 can add to or subtract from the field created by the magnet pole pieces. The magnitude of the current through the coils 124 determines the strength of the field added to or subtracted from the field due to the magnet pole pieces (and related yoke structure) alone.

The actual determination of the current through the Helmholtz coils is accomplished by carrying out the magnetic energy and resonance techniques hereinafter described in preliminary runs and adjusting Helmholtz current until the maximum sensitive resonance is achieved, and then setting the Helmholtz current off resonance by a given offset of about 1-3 KHz.

The major elements of electrical controls are tuner 102, including coils 100 and 101 and variable capacitors 102-1 and 102-2, resistor 102-3 and diodes 102-4 and constructed for tuning to Q of twenty to fifty to achieve coil 100 resonance, and control 104 including a transmit/receive switch 104-1, a transmitter 104-2 and receiver 104-3, a crystal oscillator 104-4, gated pulse generator (PPG) 104-5, and phase shifter 104-6. The crystal provides a nominal twenty Megahertz carrier which is modulated or demodulated by the MOD, DEMOD elements of transmitter 104-2 and receiver 104-3. The receiver includes variable gain amplifier elements 104-31 and 104-32 for operation. The analog signals received are fed to a high speed at least 12 bit flash A/D converter 105-1 and internal (to the instrument) CPU element 105-2, which provides data to an external computer 106 which has a keyboard 108, monitor 110, modem 109, recording elements 112 and process controller elements 114, e.g., for control of valves V1, V2 via valve controls 115 and/or to coil current controls 122, all via digital-analog converters (not shown).

The analog signal FID curve is conditioned by a Bessel filter which acts as a pre-filter and an anti-aliasing filter as the subsequent sampling is done at 10 MHz which is half the folding frequency of the system. After digitization the signal is time smoothed by a fast Fourier transform filter program. The combination of these filters is a relative improvement in signal to noise ratios which enhance the accuracy of the system.

The excitation of coil 100 and excitation-precession of the sample's proton content and subsequent relaxation/decay produces a received FM signal that, after demodulation, controlled gain amplification, A/D conversion and plotting of points has the free induction decay (FID) curve shape C shown in FIG. 3.

FIG. 3, voltage-time trace, shows the elements of a "cycle" (with (+) and (−) sub-cycles) of excitation of a sample and free induction decay. In each (+)/(−) sub-cycle a pulse of excitation energy is applied. The excitation pulse center is taken as t0. The transceiver 104 electronic components do not receive effectively until saturation effects are overcome at t1. Then a useable curve C(+) or (C−) is developed. The signal processing equipment can add or subtract consecutive C+ and C− forms for useful adjustment as described below.

The FID curve data is stored in the external computer 106 where a program finds the best curve to fit each stored FID curve. The FID curve C has three primary component parts shown as A, B and E in FIG. 3. The A curve which dominates the first part of the FID curve is an Abragam curve while the B curve that dominates the middle part of the curve is a slower Gaussian(i.e. slower than the Gaussiancomponent of the Abragam), and E that dominates the later part of the FID curve is an exponential decay. The Abragam and exponential portions are respectively controlled by bound and unbound proton content of the samples, (e.g., (1) water of hydration molecules and other water (moisture) content of the sample mass, (2) crystalline and amorphous contents where they both occur, including mixtures of highly and lightly polymerized materials and (3) components of a mixed elastomer-polymer). The slower Gaussianis a transition zone between the two and is controlled by protons which are partially bound or those in a state of becoming unbound. The determination of the type of curves which makes up the FID curve C is important because once the curves are known they can be extended back to a time origin (shown as $A_o$, $B_0$ and $E_0$ at t0, i.e., excitation of a Cycle 1), which is close to the center of the transmitted burst signal. This is important since there are saturation effects of the instrument's electronic gear which occur during and after the burst signal to t1. During this time measurements cannot be accurately taken, yet the area of interest under the curve, which is a measure of the number of nuclei in the sample, extends from t0 to t4 beyond which the curve is too small to matter and the electronics need recovery time to prepare for the next cycle (beginning with a pulse centered at t#02).

Since the system is offset from resonance, the received frequency signal as the sample goes through relaxation is a damped oscillation signal (whereas at resonance the signals are effectively undamped over the time of interest). This damping signal is a cosine signal which is active over the entire FID and is used in the curve determination as hereafter discussed. Operation at resonance is difficult since many factors can bring the system out of resonance easily whereas operation at near resonance is relatively easily achieved and maintained. The near resonance operation of the system still yields good results since small variations of frequency near resonance cause only minor secondary effects.

Each (sub) cycle goes on to t5 to allow for recovery i.e., essentially full relaxation of the protons of the sample before beginning a new transmit signal burst (t0#2). Typically, an excitation pulse interval is five to ten microseconds, the t0–t1 time is five to fifteen microseconds (the shorter the better), t1–t2, where effects due to bound nuclei (Abragam) are predominant, is five to fifteen microseconds duration (with critical measurement taken at a narrower region tm); t2–t3 is a transition region of fifteen to twenty-five microseconds duration characterized by phase cancellation effects, and t3–t4 is a region where the unbound (exponential) component predominates. It lasts from one hundred to five hundred microseconds.

The entire FID curve is composed of several major components as shown, e.g., in Equation (Eq.) 1 as applied to polyethylene and like materials analysis, although as described there may be fewer components on some occasions. Furthermore, as mentioned before, functions other than Abragam, Gaussian or exponential may be present in addition to or in lieu of one or more of these components, e.g., $Ce^{-(kt)^\alpha}$ (known also as a modified exponential) where $\alpha$ lies between 0 to 1 or 1 to 2, and these additional components can have a strong influence on the overall FID curve in early, mid or late time (+) portions of a decay cycle.

Eq. 1: $F(t) = [\cos(\Delta ft)][[Abragam] + [slower Gaussian] + [exponential]]$ The entire curve is fitted by an iterative process based upon the Marquardt-Levenberg (M-L) approximation technique applied automatically through a structured realization in software. This technique is used to determine the magnitude of all the parameters, constants, frequencies, etc. contained in Eq. 1 which best fit the FID curve—to some given error range. This is an iterative technique where the entire curve is determined at once. The M-L technique is documented in the following references: *Ind. Appl. Math.*, vol. 11, pp. 431–441 by D.W. Marquardt 1963; *Data Reduction and Error Analysis for the Physical Sciences* (New York, McGraw Hill), Chapter 11 by Philip R. Bevington 1969; and *The State of the Art in Numerical Analysis* (London: Academic Press, David A.H. Jacobs, ed 1977), chapter III.2 by J.E. Dennis. As applied to the measurement regime of interest herein in a preferred embodiment of the present invention the selected parameters are the y-axis intercept ratios and time constants, temperature coefficients, frequency terms and other parameters described below.

We have established that there are approximate limits placed upon the technique which constrain the coefficients to a limited range for the types of samples being investigated described above and for samples of the type described herein, if the technique is not converging after a given number of iterations, 30 in the preferred embodiment, that sample is discarded. In addition the technique fails in utilization in a cosine mode with M-L since M-L fails for a cosine frequency term of zero when the system is in resonance. This last fact is an added benefit since keeping the system in resonance is very difficult where being out of (but near) resonance is relatively easy as previously discussed.

Once the equation of the FID curve is known, each component can be extrapolated back to t0 to establish the intercept of each said component.

There is a final t4–t5 region, for allowing recovery (re-equilibration) of the sample material, which can be on the order of hundreds of milliseconds up to several seconds.

The resulting data utilized in the computer 106 (FIGS. 1-2) is the equation for the FID curve as composed of the three (excluding the cosine term) components shown in Eq. 1. Each of these curves (and their intercepts) has been experimentally and theoretically related to the same nuclei of interest. In particular, when the FID curve equation is determined, the following ratios of the y-axis intercepts of the indicated curves are formed: the G/Abragam, (R1), and the exponential/Abragam, (R2). These ratios (R1,R2), the cross product (R12), together with the squares of these ratios (R11,R22), the decay times for each of the three curve components, the product temperature and the cosine term form a ten dimension model. A regression relates the curves theoretically and experimentally to the same nuclei of interest wherein some are tightly bound, others loosely bound and some in between. The results are independent of the amount of sample, and the gain of the system, which obviates the need to measure these physical quantities.

The M-L iteration process performs the curve fitting by attempting to minimize the Chi Squared function (the sum of the squared differences between the measured data points and the data points from the derived equation).

Calibration of the system is accomplished by measuring a number of known samples and using the M-L technique to derive the model equation constants associated with each known sample. Regression analysis is then performed to derive the coefficients relating the various model equation constants to the desired measured quantity or quantities. A calibration equation is then prepared using these coefficients.

In operation, an FID is obtained from the test sample and by the M-L technique the constants of the model equation are determined. These constants are then input to the calibration equation and the desired parameters are calculated.

Figure 5:
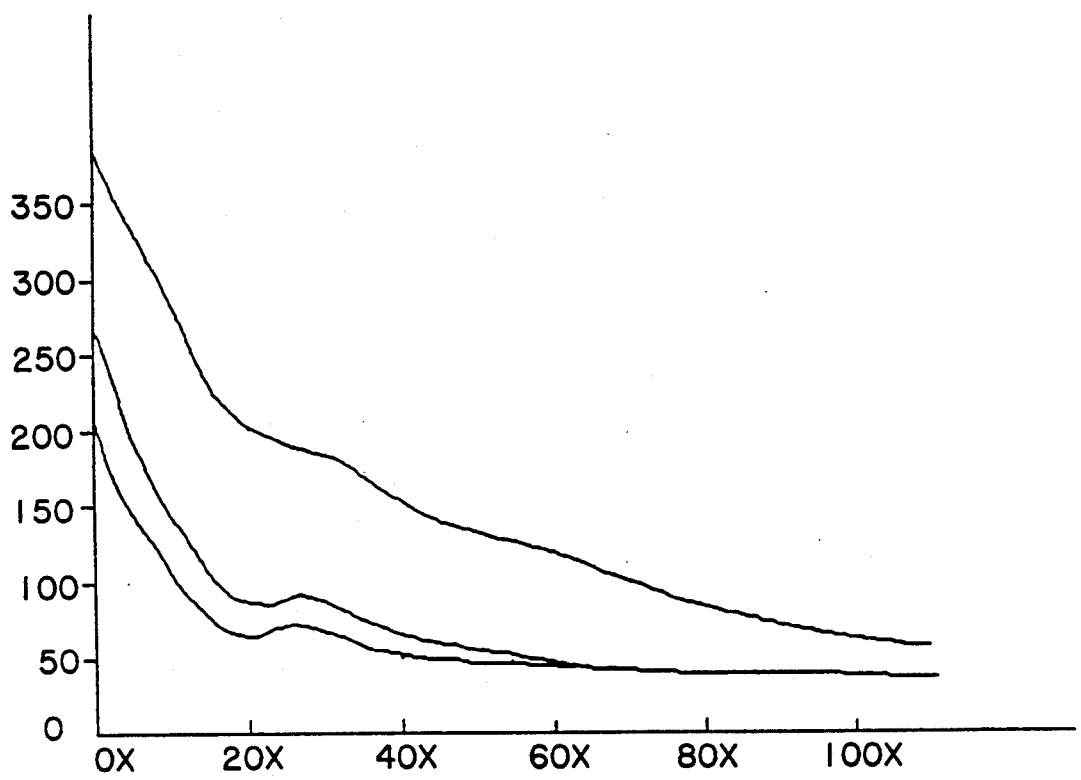
FIG. 5 is a voltage - time trace for FID curves derived from samples of different densities of polyethylene.

FIG. 5 shows FID's taken for polyethylene samples of the highest 7-1, less 7-2, and least 7-3 density. The curves are sufficiently distinct and the resulting three component parts found (by M-L) for each curve result, after regression, in values from which actual polyethylene density results can be read off using the calibration curve shown in FIG. 6.

The data can be used as a QC type measurement or as an on-line control parameter which is fed back to control a process, back in line IPL (FIG. 1) or related equipment (e.g., in drying or baking a food product, conducting a continuous chemical or metallurgical reaction process, etc.).

The form of the input operating parameters of the system can be wide reaching to include previously stored parameters in PROMs or ROMs or in magnetic storage media such as disks or tapes or inputs sent in over telephone line and modem 109. The generation of the excitation pulse can be accomplished with many techniques including a coil or antenna arrangement. The steady magnetic field can be generated by electromagnets, permanent magnets, electromagnetics with superconducting winding or other standard techniques of generating magnetic fields.

Figure 4:
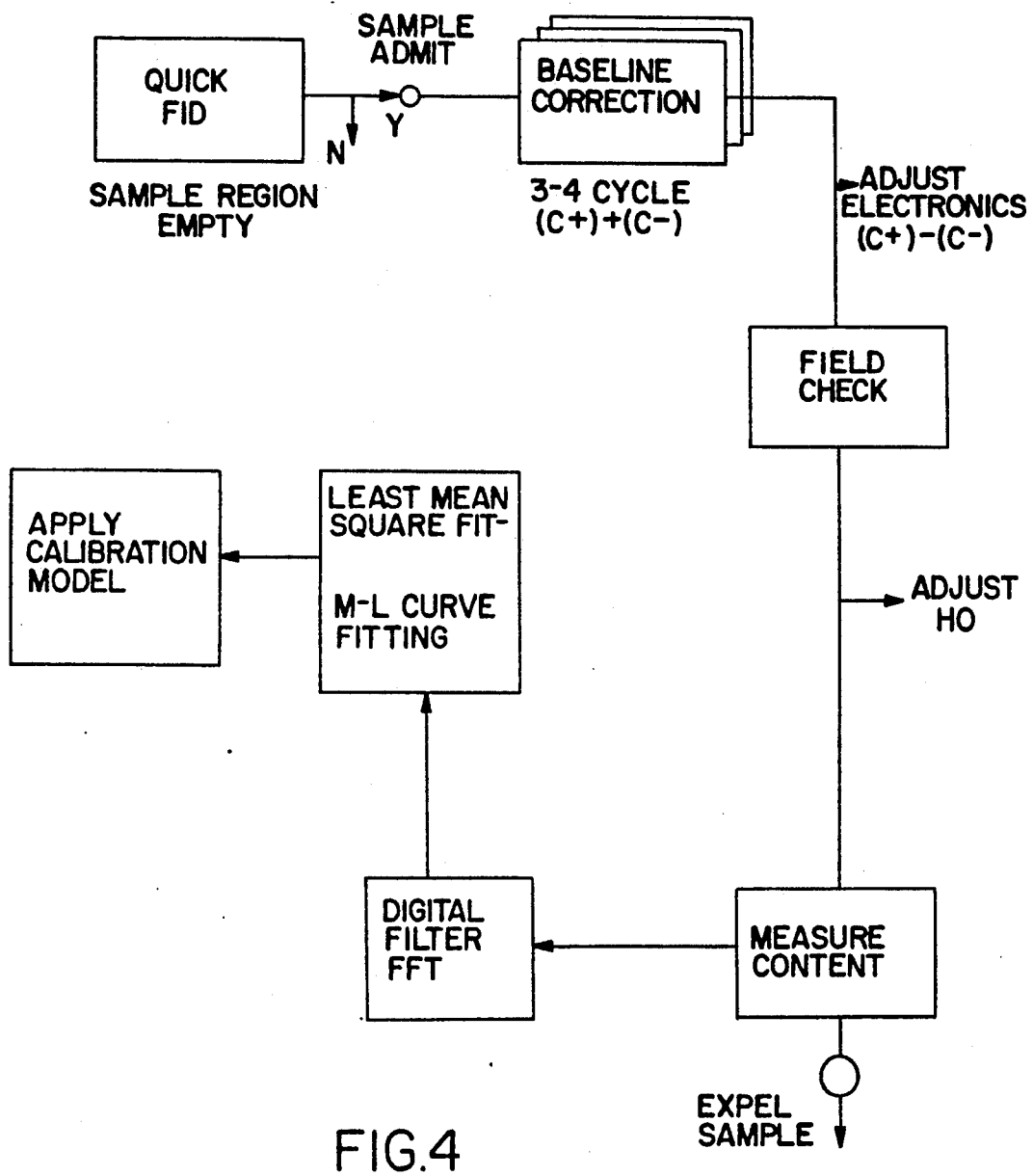
FIG. 4 is a flow chart of measuring steps utilizing the FIGS. 1-2 apparatus including its signal processing elements, (the activity of which is illustrated by the FIG. 3 wave forms)

FIG. 4 is an expanded flow chart showing the steps of measurement to establish effective industrial measurement. First a single free induction decay curve C is established to see if the sample area is clear (Quick FID) in an abbreviated cycle of attempting to establish a curve C. If the sample region is not clear (N), measurement is interrupted to allow valve V2 (re)opening and operation of jets J and gravity to clear the region. A new Quick FID step establishes clearance. Then a sample is admitted by closing valve V2, opening valve V1 and making such adjustments of probe P and line LI as may be necessary (if any) to assure sample acquisition. Jets J adjust and stabilize the new sample.

Temperature controls 134–138 and 142–146, described above, establish very coarse and less coarse thermal controls countering sample temperature variations.

An electronic signal processing apparatus baseline is established in 3–4 cycles (each having (+) and (−) sub-cycles with addition of (C+) and (C−) to detect a base line offset and compensate for it). It would be feasible to avoid this baseline step phase determination and simply deal with it as an additional (i.e. eleventh dimension in the M-L analysis, but this would increase iteration time).

Further adjustment is established by coils 124 to adjust H0 and this is enabled by ten to twenty field check cycles of FID curve generation. The (C−) FID is subtracted from the (C+) FID, i.e., the absolute C values are added to obtain a workable digitized FID signal—which has a maximum value at resonance. H0 is adjusted via coil current generator 117 and coils 124 until such maximum is achieved, and then H0 is changed to offset the system a known amount from resonance. These measurements are taken in a reliable region for such purpose, i.e., the exponential region of t3–t4 (the above baseline measurements are also taken there). Adequate field adjustment is usually made in less than seven cycles.

Then five to one hundred cycles are conducted to obtain a useable measurement. Each of those five to one hundred cycles involves a modulated transmission/reception/flash A-D conversion, and storage of data. The curves are then averaged for M-L curve fitting, and the above listed intercepts and ratios are established. Similar cycles, but somewhat abbreviated can be applied for Quick FID, field check and baseline correction purposes. Each of the sub-cycles [(+) and (−)] of each such cycle involves a capture and utilization of thousands of FID points in data reduction. Each sub-cycle occurs on the order of a second and the number of such sub-cycles employed depends on the desired smoothing and signal to noise ratio (S/N); generally S/N improves in a square root relationship to the number of samples.

As noted in above cited Dechene et al. patents, in requiring greater accuracy and reliability, sample tube composition can distort readings. If glass is not used (and it is preferred to avoid glass in industrial usage), then the replacement should not be a hydrocarbon plastic. But fluorocarbons can be effective in several applications since signals from fluorine appear far from resonance. These signals can be distinguished from hydrogen at the levels of sensitivity required and if desired can be filtered (or distinguished). In other cases of higher sensitivity measurements, e.g., for gauging relative proportions of amorphous and crystalline species in mixtures thereof, the sample container should be glass or non-protonic ceramic. In some instances, however, fluorocarbon or reinforced fluorocarbon can be used acceptably for polymer measurements. In all such cases the point is to avoid sample containers with species that can couple with transmitted energy and generate a FID decay curve mimicking the samples.

FIG. 5 shows FID curves for polyethylene sample of highest, less and least density. The curves are sufficiently distinct so that the differences are detectable by the signal processing means described above.

Since the regression analysis involves ten variables residing in an eleven dimensional space the results cannot be graphed. But the measurements obtained from the model represented in the present invention can be favorably compared to the results obtained from accepted off-line measuring techniques.

Figure 6:
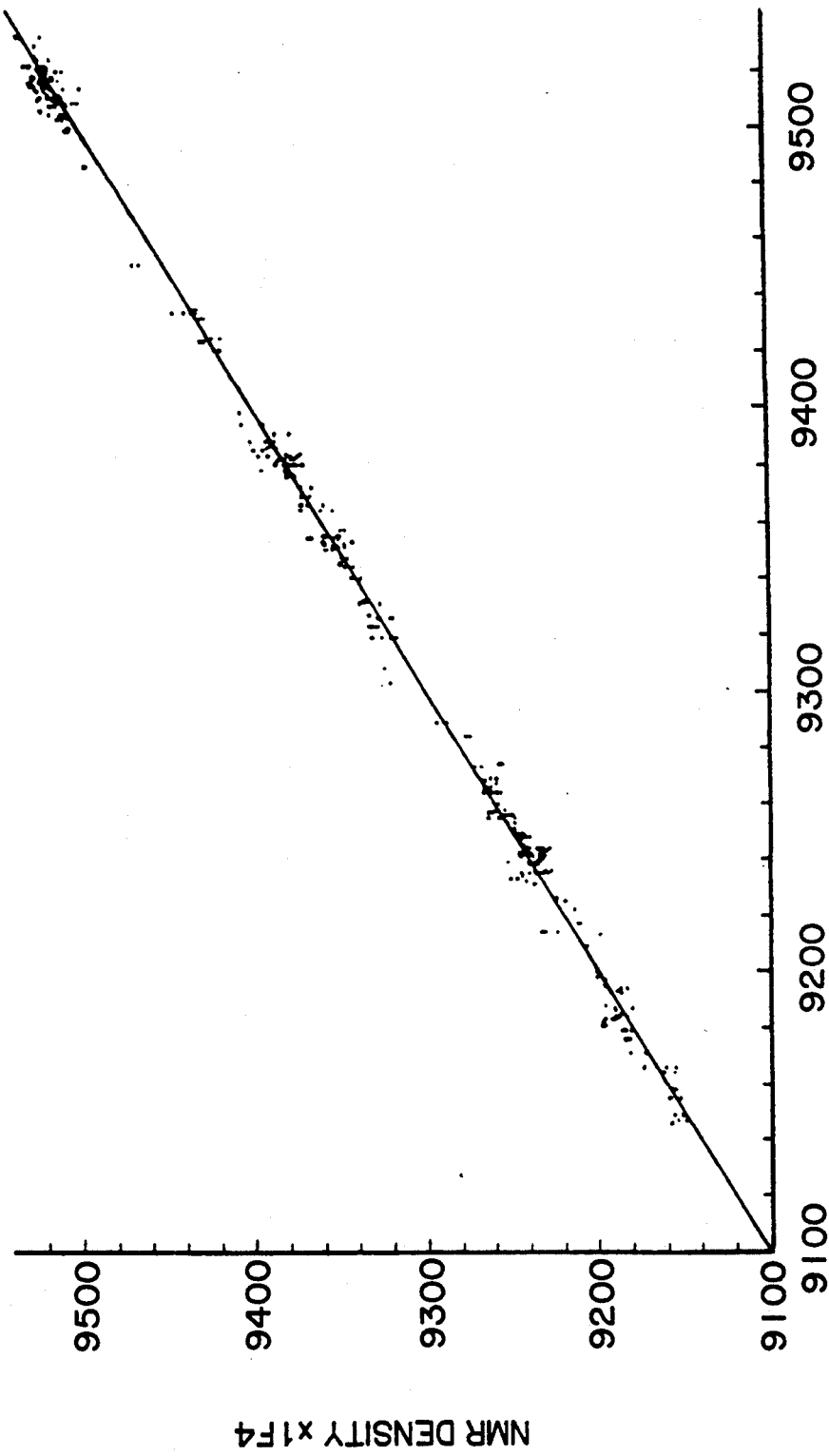
FIG. 6 is a calibration curve for absolute density measurement for polyethylene useful with the FID's from FIG. 5.

FIG. 6 shows a calibration curve of such polyethylene density measurements by the present invention (y axis) vs. standard method (e.g. oil bath flotation) density measurements (x axis), illustrating the efficacy of the present invention. Similar results are obtained with other standard methods such as acoustic transmissivity.

Figure 7:
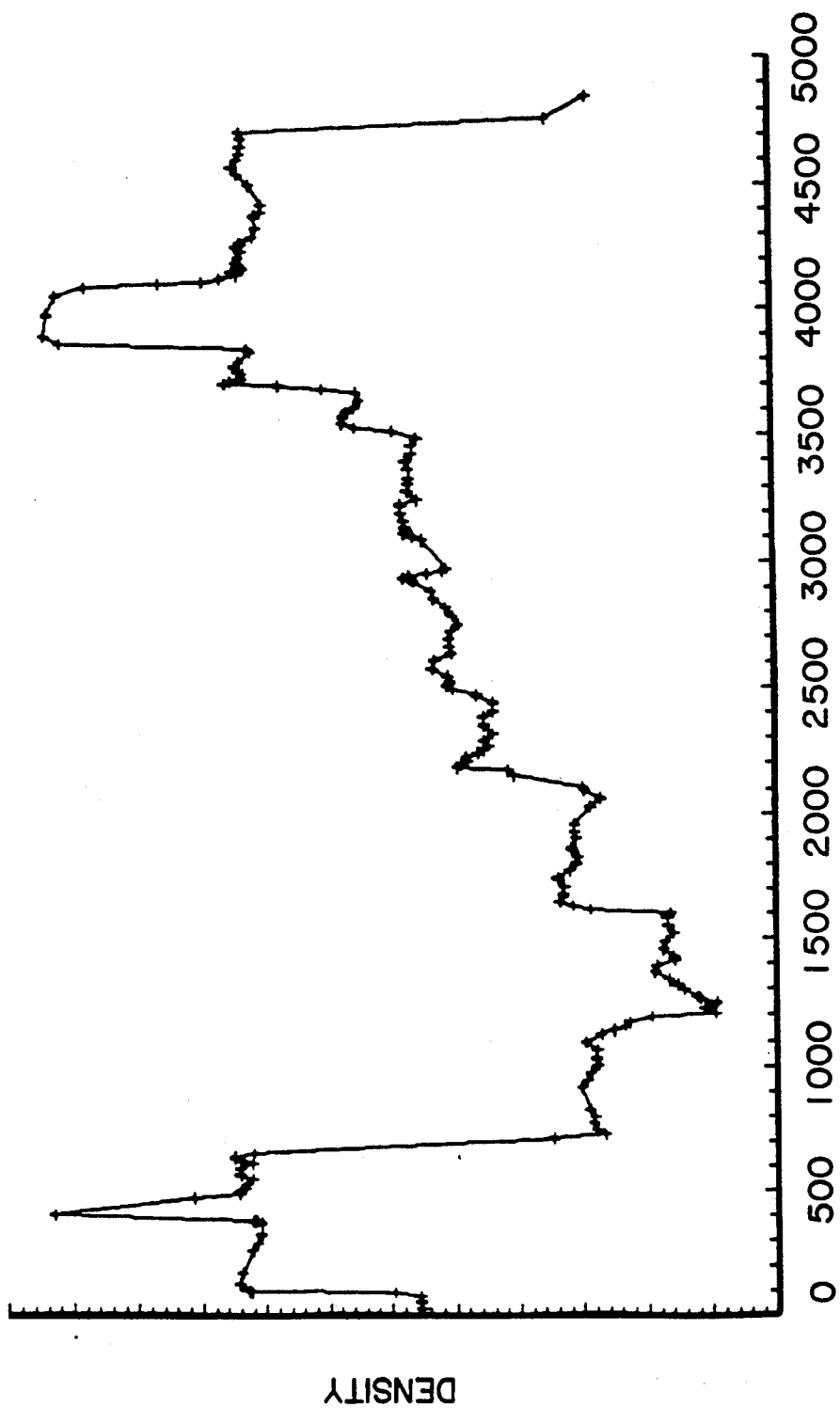
FIG. 7 is a graph of the calibration data from off-line laboratory measurements of polyethylene.
Figure 8:
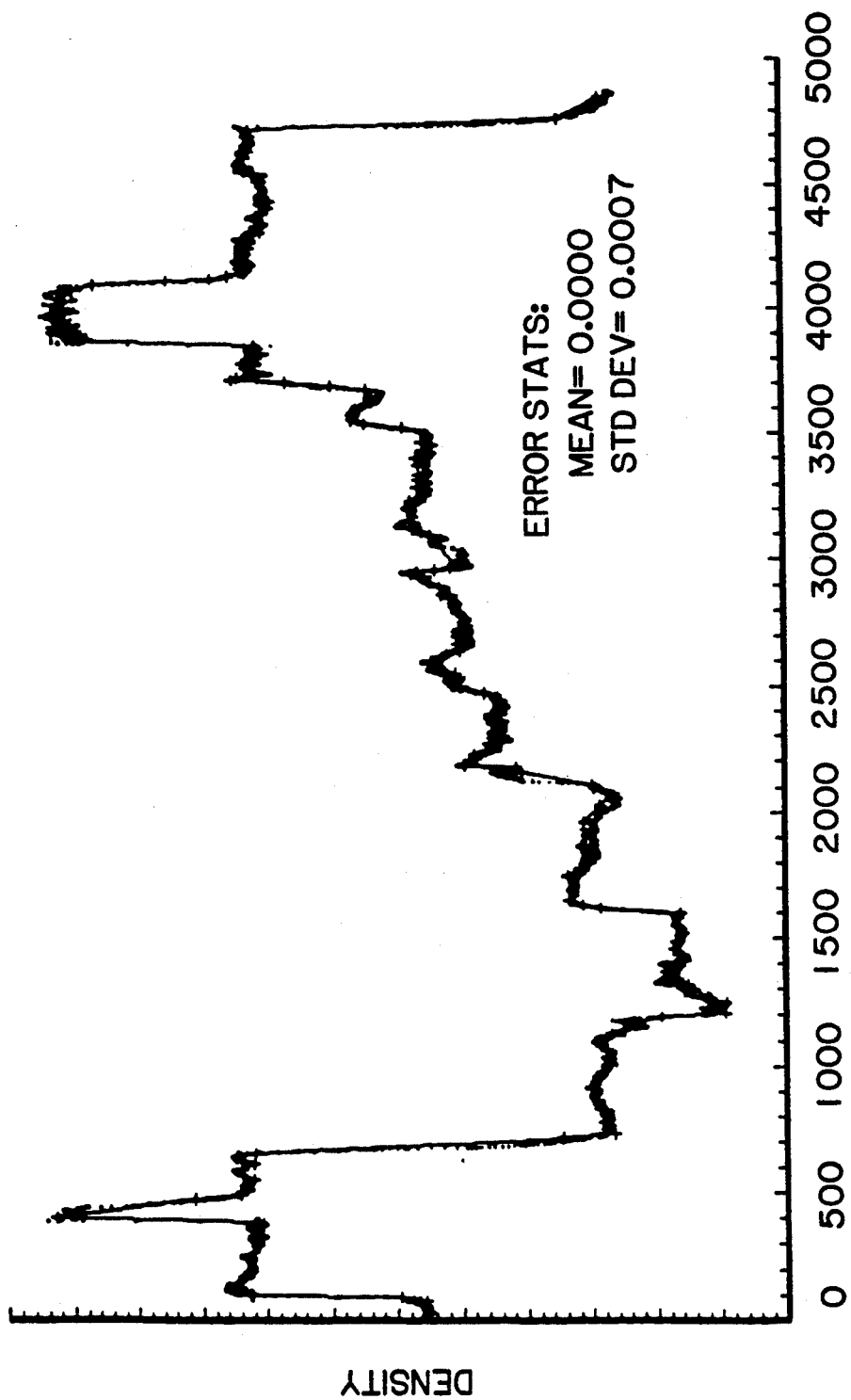
FIG. 8 is a graph superimposing data points measured by NMR and the laboratory data of FIG. 7.
Figure 9:
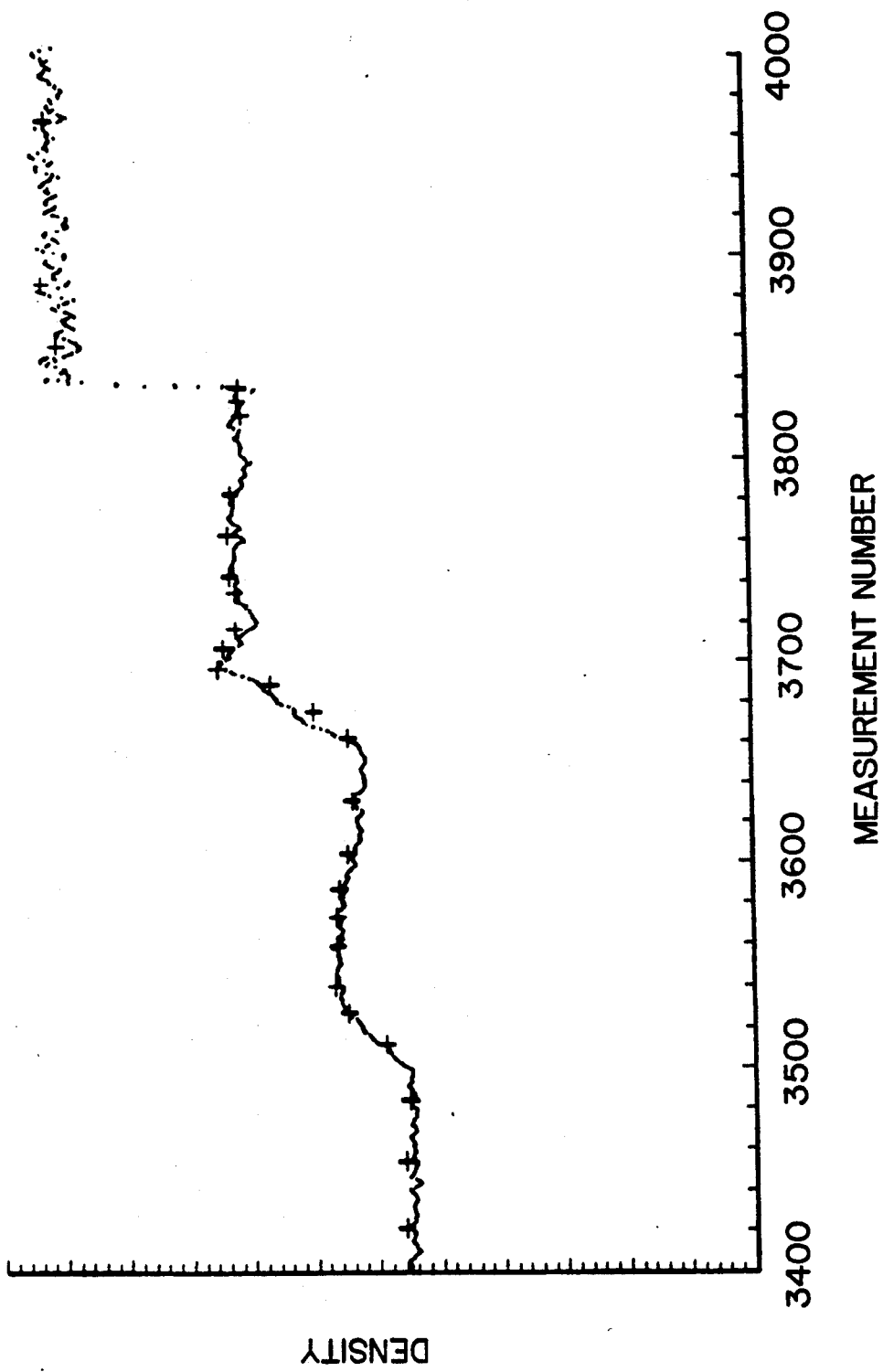
FIG. 9 is an expanded graph of the transition range of FIG. 8.

FIG. 7 graphs 350 data points measured by standard off-line laboratory methods; FIG. 8 adds 5000 data points measured by the disclosed NMR techniques of the present invention to the FIG. 7 data points; and FIG. 9 details the transition area of FIG. 8. In these examples the accuracy of the present invention is illustrated.

As noted above at E8. 1 and surrounding text there can be several other embodiments of application of the system and process described herein including, e.g. (a) use of a mode other than cosine mode described above (e.g. sine mode); (b) x-base parameters other than time; (c) use of other selected FID curve portion forms, e.g. a modified exponential as mentioned above, in lieu of or in addition to one or more of the Abragam, Gaussian and exponential components; and (d) other iterative/regression techniques than those described above in relating selected key parameters for a material and consequent form of the selected curve portion to a best fit with the measured curve.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. Magnetic resonance system for industrial process monitoring of the number of bound (Abragam), intermediately bound (slow Gaussian) and unbound (exponential) magnetically active nuclei in a sample, by exciting these nuclei and measuring the sample relaxation free induction decay of said nuclei, comprising:
    (a) means for accessing and removing successive samples of material from an industrial process, placing them in a sample measuring region and discarding successive samples from said region,
    (b) means for applying a base magnetic field to said region to effect precession on sample magnetically active nuclei therein and means for applying a local excitation pulse to said region to modify the precession, wherein said excitation pulse comprises frequency characteristics offset from resonance, by more than 0.1 KHz,
    (c) means defining receive antenna coil means and signal translating means interacting with the sample to detect the sample relaxation free induction decay to form an electronic signal over time from said free induction decay indicating the form of decay,
    (d) means for establishing a digitized version of the electronic signal indicator of free induction decay and means for analyzing the electronic signal to components of the electronic signal, said components including, in time sequence, Abragam, slow Gaussian and exponential portions, said means for analysis comprising:
    means for determining the time equation of each of said electronic signal components, and establishing zero intercepts, and time constants of said electronic signal components, from which the number of bound (Abragam), intermediately bound (slow Gaussian), and unbound (exponential) magnetically active nuclei are determined.

2. A system as defined in claim 1 wherein said means for determining the time equation comprises means utilizing a Marquardt-Levenberg iteration for establishing said zero intercepts and time constants.

3. A system as defined in claim 1 wherein means for analyzing the electronic signal components corresponding to quantities of target nuclei of the sample materials comprises: means for establishing calibration curves wherein the zero intercepts and time constant constants of said electronic signal components of standard samples are related to the known physical quantities of target nuclei in said standard samples, and means for comparing said calibration curve to zero intercepts and time constants of an unknown sample wherein said physical quantities of nuclei of interest are read from the calibration curve.

4. A system as defined in claim 3 wherein said means for comparing said calibration curves to the electronic signal of an unknown sample comprises a regression analysis.

5. A system as defined in claim 1 further comprising:
feedback means to effect a constant thermal environment for said sample measuring region, wherein thermal drift components are nullified.

6. A process for monitoring industrial processes utilizing magnetic resonance comprising:
accessing and removing successive samples of material from said industrial process,
placing said samples in a sample measuring region,
applying a base magnetic field to said region to effect precession on sample nuclei therein,
applying a local resonant excitation pulse to said region to modify the precession,
receiving and translating the free induction decay from the relaxation of the sample nuclei and forming an electronic signal therefrom,
digitizing the free induction decay and analyzing it to components of the electronic signal corresponding to quantities of target nuclei in the sample materials, said analyzing comprising:
determining the time equation of said electronic signal components
establishing zero intercepts and time constants from said electronic signal components,
relating said zero intercept and time constants to the quantity of bound (Abragam), intermediately bound (slow G) and unbound (exponential) nuclei, and
discarding said sample from said region.

7. A process as defined in claim 6 wherein the determination of the time equation of the digitized electronic signal comprises:
applying a Marquardt-Levenberg iteration technique to the digitized decay curve wherein said digitized electronic signal is separated into an Abragam, a slow Gaussian and an exponential component.

8. A process as defined in claim 6 wherein relating the zero intercepts and the time constants to the quantity of target nuclei of the sample materials comprises:
generating calibration curves relating the zero intercepts and time constants of the electronic signal components of standard samples to known quantities of target nuclei in said standard samples, and
comparing said zero intercepts and time constants measured from an unknown sample to said calibration curve wherein said quantities of nuclei of interest contained in said unknown sample are read from the calibration curve.

9. A process as defined in claim 8 wherein said means for comparing said calibration curves to the electronic signal of an unknown sample comprises a regression analysis.

10. A process for monitoring industrial processes utilizing magnetic resonance to measure the number of bound, intermediately bound and unbound magnetically active nuclei in a sample, by exciting these nuclei and measuring the nuclei relaxation free induction decay of said nuclei comprising:
accessing and removing successive samples of material from said industrial process,
placing said samples in a sample measuring region,
applying a base magnetic field to said region to effect precession on sample nuclei therein,
applying a local resonant excitation pulse to said region to modify the precession and produce a free induction decay,
receiving and translating the free induction decay from the relaxation of the sample nuclei to form an electronic signal over time from said free induction decay,
digitizing the electronic signal and analyzing it to components of the electronic signals corresponding to quantities of target nuclei in the sample materials, said analyzing comprising;
determining the time equation of the electronic signal,
establishing zero intercepts and time constants from said equation,
storing general forms of electronic signals and key parameters thereof,
applying a selected one or more general forms of electronic signal formulas with key parameters related to the material under study to portions of the measured free induction decay, utilizing an iterative process of application of said key parameters of the selected forms and therefore electronic signal components based on said forms until a predetermined best fit where the measured electronic signal is attained and striving for said key parameters that produce the best fit,
discarding said sample from said region,
and applying said stored parameters as a measure of the material.

11. A process as defined in claim 6 wherein the selected general forms of electronic signals comprise two or more of Abragam, Gaussian, exponential and modified exponential forms.

12. A process as defined in claim 11 wherein the forms comprise Abragam and stretched exponential only.

13. A process as defined in claim 11 wherein the forms comprise all of Abragam, Gaussian, exponential and stretched exponentials.

14. A process as defined in claim 10 wherein Marquardt-Levenberg iteration is utilized.

15. The apparatus as defined in claim 21 wherein said excitation pulse comprises frequency characteristics offset from resonance by an amount within the range 1 to 3 KHz.

16. A system as defined in claim 15 wherein the selected general forms of electronic signal comprise two or more of Abragam, Gaussian, exponential and modified exponential forms.

17. A system as defined in claim 15 wherein the forms comprise Abragam and stretched exponential only.

18. A system as defined in claim 15 wherein wherein the forms comprise all of Abragam, Gaussian, exponential and modified exponentials.

19. A system as defined in claim 15 wherein Marquardt-Levenberg iteration is utilized.

* * * * *

UNITED STATES PATENT OFFICE
CERTIFICATE OF CORRECTION

PATENT NO. : 5,302,896

DATED : April 12, 1994

INVENTOR(S) : Ronald L. Dechene, et al.

It is certified that error appears in the above-identified patent and that said Letters Patent is hereby corrected as shown below:

In column 14, line 54, change as follows:

FROM:

15. The apparatus as defined in claim 21 wherein ...

TO:

15. The apparatus as defined in claim 1 wherein...

Signed and Sealed this

Thirtieth Day of August, 1994

Attest:

BRUCE LEHMAN

Attesting Officer

Commissioner of Patents and Trademarks